United States Patent [19]

Schuck et al.

[11] Patent Number: 4,804,632

[45] Date of Patent: Feb. 14, 1989

[54] METHOD FOR DETECTING COMBUSTIBLE GASES AND DEVICE THEREFOR

[75] Inventors: Hansjochen Schuck, Stockelsdorf, Fed. Rep. of Germany; Peter J. Iredale, Seghill; Alan Johnson, Sunderland, both of Great Britain

[73] Assignee: Drägerwerk Aktiengesellschaft, Lübeck, Fed. Rep. of Germany

[21] Appl. No.: 6,695

[22] Filed: Jan. 21, 1987

[30] Foreign Application Priority Data

Jan. 21, 1986 [GB] United Kingdom ............... 8601388

[51] Int. Cl.⁴ ...................... G01N 27/16; G01N 27/18
[52] U.S. Cl. ........................................ 436/143; 73/23; 73/27 R; 422/94; 422/95; 422/96; 422/97; 436/141
[58] Field of Search ................................ 73/23, 27 R; 422/94–96, 98, 97; 436/139, 143, 141

[56] References Cited

U.S. PATENT DOCUMENTS

| | | | |
|---|---|---|---|
| 2,010,995 | 8/1935 | Jacobson | 422/95 |
| 2,720,108 | 10/1955 | Johnson | 422/94 X |
| 4,258,002 | 3/1981 | Barr | 422/95 |

FOREIGN PATENT DOCUMENTS 1673306 6/1971 Fed. Rep. of Germany.

Primary Examiner—Barry S. Richman
Assistant Examiner—Timothy M. McMahon
Attorney, Agent, or Firm—Walter Ottesen

[57] ABSTRACT

A method detects the proportion of combustible gas in a mixture of air with a measuring device which operates by both the heat-tone and heat-conductivity methods. The method permits measurement in the full concentration range with a high degree of accuracy and the lowest possible energy consumption. The measuring device is made small and light and its sensor has a long service life. The method uses one single sensor which operates at a low temperature in the heat-conductivity mode or alternatively, catalytically active at a higher temperature in the heat-tone mode. If the measurement provides a result below a reference value or within a reference value window, measurement continues in the more accurate heat-tone mode. When the gas concentration increases during measurement, in order to avoid ambiguity of the measuring signal and damage to the sensor above a load-limit value, measurement again takes place in the heat-conductivity mode by reducing the temperature of the sensor.

10 Claims, 2 Drawing Sheets

METHOD FOR DETECTING COMBUSTIBLE GASES AND DEVICE THEREFOR

FIELD OF THE INVENTION

The invention concerns a method of detecting the proportion of combustible gases in a mixture of air with the aid of a measuring device fitted with an indicator unit which operates by both heat-tone and heat-conduction methods and only gives a heat-tone method reading below a predetermined reference value for the measuring signal. A measuring device to apply the method is also provided.

BACKGROUND OF THE INVENTION

For the detection and measurement of combustible gases it is preferable to utilize gas sensors which contain a catalyst and are heated to a specific temperature (for example 500° C.) which will cause the combustible gases to burn catalytically on the surface of the sensor by consuming part of the oxygen present in the measuring gas and to raise the temperature of the sensor. The heat-tone effect generated during the combustion reaction is analyzed and indicated by means of the sensor temperature increase as a measuring signal for the concentration of combustible gas in the air mixture under test. The measuring device for this is generally an active detector and passive compensating sensor in a half arm bridge arrangement. This bridge is fed with either constant current or constant voltage. This type of measuring device operates satisfactorily up to concentrations of 100% LEL (Lower Explosion Limit) of the combustible gas in air. In the case of methane, for example, this limit is 5% by volume. Above this value, a temperature increase in the detector, residual activity in the compensator, oxygen reduction and thermal conductivity changes in the gas mixture all lead increasingly to a non-linear measuring signal with reference to the gas concentration. For gas concentrations in a range above 100% LEL, the bridge output signal does not remain unambiguous, that is, two gas concentrations are found per output voltage value. In order to achieve unambiguous measurements of concentrations over 100% LEL, the measurement bridge used may, for example, be given another arm. This also measures in a bridge arrangement at a reduced operating temperature of, for example, 200° C. only the change in the thermal conductivity of the gas mixture around the sensor. When a specific threshold value for thermal conductivity, which may be in the range of 100% LEL, is reached, the indicator connected to the zero arm of the heat-tone measurement bridge is automatically switched over to full-scale reading via a suitable control element. This gives an indication that the gas sample contains a concentration of combustible gases of over 100% LEL.

This type of measuring device and the method of switching between heat conduction and heat-tone measurement is described in published German patent application DE-OS 16 73 306.

In the case of the measuring device already known, to measure methane in air, for example, one sensor is kept in the heat-tone measuring bridge at an operating temperature of around 500° C. and another sensor is kept in the heat-conduction measurement bridge at an operating temperature of, for example, 200° C. In the measuring range up to 100% LEL the sensor in the heat-tone measurement bridge gives an unambiguous signal. Above the limit of 100% LEL, the measuring instrument in the zero arm of the heat-tone measurement bridge is indeed switched to full-scale reading, but the current or voltage supply of the heat-tone sensor is retained. If the methane content in the air mixture increases further above 100% LEL, the combustion heat on the surface of the catalytic heat-tone sensor increases to such an extent that the consequence may be thermal destruction of the catalyst layer, or at the very least, a substantial reduction in the usability of the sensor for further measurements. There is no point either in switching off the heating current to reduce the operating temperature of the sensor since at these high concentrations catalytic combustion carries on of its own accord and continues either until the gas concentration falls or until the catalyst is contaminated and/or the sensor destroyed.

After switchover of the indicator in the zero arm of the heat-tone measurement bridge to full-scale reading, measurement of the concentration of the actually detectable harmful substance present in the air mixture is no longer possible.

In the case of the measuring device already known, two measurement bridges have to be simultaneously and continuously supplied with electric power; and in particular, both sensors in the measurement bridges have to stay heated to 200° C. or 500° C. in order to guarantee constant measurement readiness. This means increased power consumption because both sensors must be simultaneously maintained at their respective operating temperatures, although only one of them would be required for actual measurement or for fixing the time for switchover of the measuring instrument to full-scale reading. Given the necessary charging time of a measuring instrument, this increased power requirement demands a suitably adapted power supply and in the case of a portable measuring instrument, for example, necessitates carrying around large, heavy and therefore cumbersome batteries.

SUMMARY OF THE INVENTION

It is an object of the invention to improve the known method of detection of combustible gases so that an unambiguous measurement of the combustible gas in air in the total concentration range of 0 to 100% by volume is possible with the lowest possible power consumption. In addition, measurement accuracy in the lower measurement range to approximately the Lower Explosion Limit should be particularly high. A measuring device which can be operated pursuant to this type of improved method should be smaller, lighter, easier to maintain and have fewer parts. The life of the detection element should be increased.

The object of the invention is achieved with a method which uses a single sensor element which is catalytically active at higher temperatures. At the start of measurement, the sensor is held constant at an initial temperature $T_1$ which is sufficient for heat-conductivity measurement, the resultant measuring signal is compared with a reference value $R_1$ and, if it falls below the reference value $R_1$, the temperature of the sensor is increased to a second temperature $T_2$ which enables heat-tone measurement and the temperature is held constant at this value and the measuring signal emitted by the sensor is compared with a load-limit value G corresponding to a higher gas concentration than $R_1$ and its temperature is reduced to temperature $T_1$ and held constant as soon as the measuring signal exceeds the limit value G.

When the sensor is put into operation, the first stage of the process is a check on whether combustible gas is present at all. This may be carried out by setting the sensor to heat-conductivity measurement at a low operating temperature $T_1$ which uses very little electric power. If the resultant measuring signal indicates that combustible gas is present in concentrations less than the value corresponding to $R_1$, the sensor operating mode is switched over to heat-tone measurement and its operating temperature increased to $T_2$. Heat-tone measurement can be carried out more accurately than heat-conductivity measurement and the concentration of combustible gas in the air mixture is indicated more accurately. The reference figure $R_1$ can thus be seen as a threshold value which marks the presence of combustible gases and switches the sensor over in good time, and in any event before the Lower Explosion Limit of the gas mixture is reached, when such low concentrations of combustible gas are present, to the more accurate heat-tone measurement which cannot cause damage to the sensor. When the sensor is in the heat-tone measurement operating mode, the measuring signal emitted is compared with a load-limit value G. As long as the measuring signal remains below the limit value G, the sensor remains in the heat-tone measurement operating mode. If, for example, with rising gas concentration, this limit value G is reached, the sensor is switched over to the heat-conductivity measurement operating mode and the lower operating temperature $T_1$ associated therewith. With further increasing concentrations of gas, measurement continues to be carried out in this mode and the measured values can be definitively assigned to the corresponding gas concentrations. By fixing the limit value G, a switchover to the lower temperature $T_1$ is achieved with rising gas concentration before a self-sustaining catalytic combustion occurs, and damages or destroys the sensor even without any electric power being supplied. In the more accurate heat-tone measurement operation, the sensor is held constant at the required temperature $T_2$ without uncontrolled heating in the presence of combustible gases being possible. Switching over to the heat-conductivity measurement operating mode at the right time protects the sensor when there is an increased concentration of combustible gas from destruction of its catalytic surface which is required for heat-tone measurement. Sensor life is therefore increased and power consumption limited to the quantity required to maintain operating temperature.

It is advisable to position the reference values $R_1$ and G in the range between 100% LEL and 140% LEL. Thus all measured values below this range will be included in the heat-tone measurement method.

A related method allows for provision to be made for heat-tone measurement only to be carried out if the measuring signal falls within a window between the reference values $R_1$ and $R_2$. Thus a lower threshold value can be determined below which the energy-saving heat-conductivity measurement is carried out and the sensor is switched over to the more accurate but greater energy-consuming heat-tone measurement only when the reference value $R_2$ is exceeded.

This method is particularly advantageous when for long periods no occurrence of combustible gases in substantial concentrations, that is, above the reference value $R_2$, is expected.

The reference value $R_1$ or the load limit value G may lie at approximately 100 to 140% of the Lower Explosion Limit (LEL), the second reference value $R_2$ in the range between 2% and 5% of the LEL. Thus, the process is utilized to control advantageously the concentration range below the Lower Explosion Limit with substantial concentrations by the accurate heat-tone measurement method at an increased sensor operating temperature $T_2$ and, as soon as the Lower Explosion Limited is reached, to operate the sensor according to the heat-conductivity measurement method as a lower operating temperature $T_1$. As soon as the concentration of combustible gas drops below the Lower Explosion Limit, the sensor is automatically switched back to the heat-tone measurement method. When increased concentrations above the Lower Explosion Limit occur, this prevents the sensor when operating in the heat-tone measurement mode from being damaged or even destroyed by catalytic combustion, as its operating temperature is switched over in good time to the lower heat-conductivity measurement level. It is therefore also in a position to supply accurate measurements again in the heat-tone measurement mode when the high concentration of combustible gases has dissipated.

It may be desirable merely to trigger an indicator full-scale reading in the upper measurement range in order to indicate when danger is present.

Apart from this, an alarm system may be operated when the second limit value is exceeded.

A suitable measuring device for carrying out this method consists of a single sensor which is maintained at a predetermined temperature by means of a controllable current source; this temperature is continuously measured, checked and balanced against ambient temperature. A computer compares the sensor signal with predetermined reference values $R_1$, $R_2$ or with the load limit value G and decides, according to the magnitude of the signal, whether the sensor should operate in the heat-tone measurement mode or in the heat-conductivity measurement mode. An appropriate signal is given to the current source. It is thus possible with only a single sensor to carry out both operating modes for measuring the concentration of a combustible gas, using one measuring circuit for both operating modes.

BRIEF DESCRIPTION OF THE DRAWING

The invention will now be described with reference to the drawing wherein.

DESCRIPTION OF THE PREFERRED EMBODIMENTS OF THE INVENTION

Figure 1:
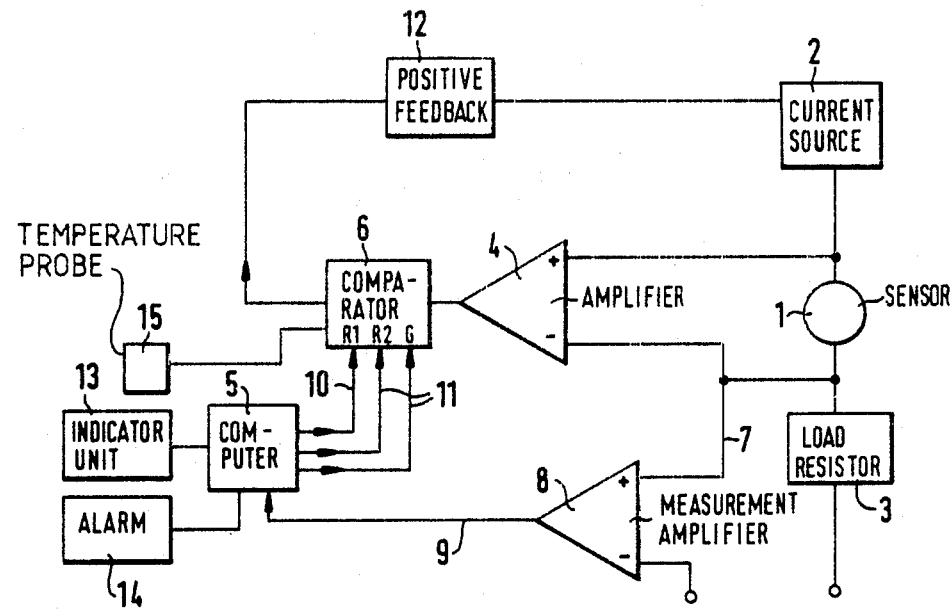
FIG. 1 is a block diagram of an embodiment of the measuring device of the invention for carrying out the method of the invention.

In FIG. 1, sensor 1 which is suitable for both heat-conductivity measurement and heat-tone measurement is connected to a controllable current source 2 and load resistance 3. The sensor resistance across the sensor 1 is measured with the aid of the amplifier 4 and converted into a temperature value in a computer assembly (5, 6). The sensor measuring signal is passed via an instrument lead 7 to the positive input of a measurement amplifier 8, the output of which is connected to the computer 5 via the signal lead 9.

Via the leads (10, 11), the computer 5 continuously interrogates the reference values $R_1$ and $R_2$ or the load-limit value G in the comparator 6. Depending on the height of the temperature of the sensor 1 and the position of the measured value in relation to the reference values $R_1$ and $R_2$ or G, the current source 2 is controlled by the comparator 6 via a feedback 12 so that it feeds to the sensor 1 the magnitude of current which is required either to maintain the temperature of the sensor 1 or to switch over between the operating temperatures for heat-conductivity measurement and heat-tone measurement. The desired value is corrected via a temperature probe 15 in dependence upon ambient temperature. The measured value determined by the computer 5 is indicated via an indicator unit 13. If the measuring signal from the signal lead 9 exceeds the load-limit value G, an alarm 14 is operated to give an audio or visual indication when the limit value is exceeded.

Figure 2:
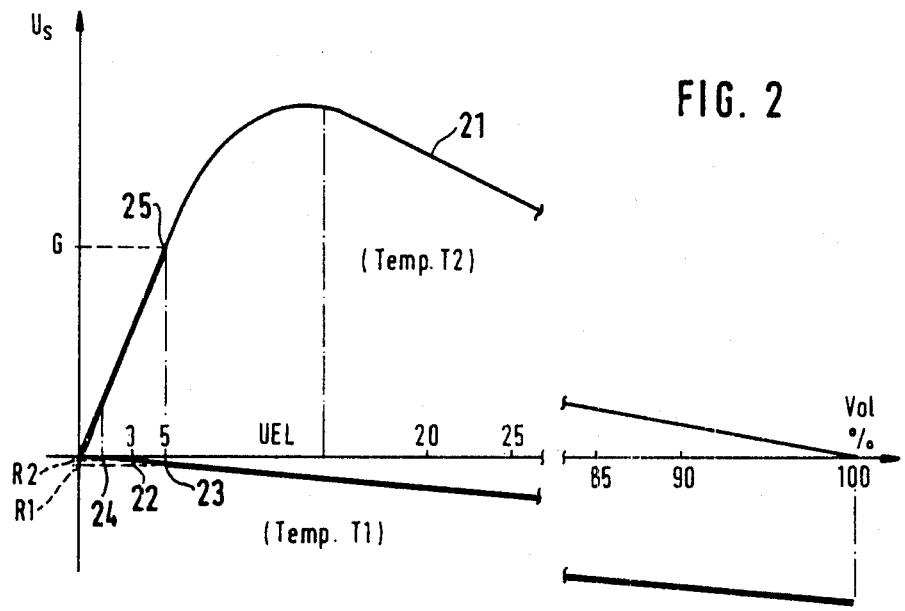
FIG. 2 is a graph of heat-tone and heat-conductivity measurements.
Figure 3:
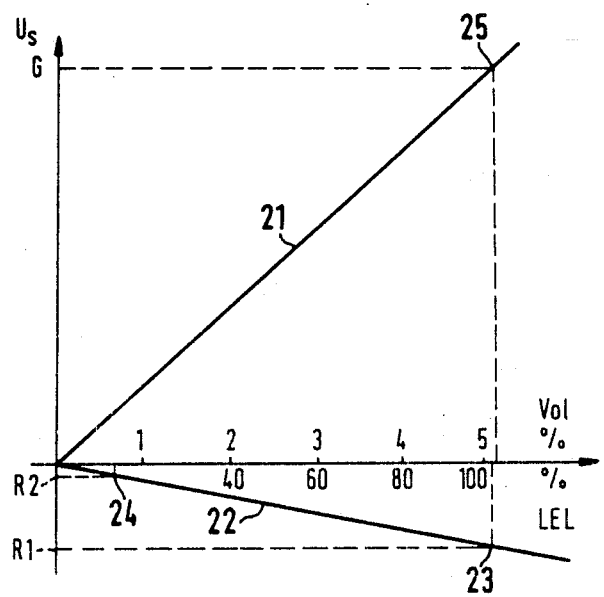
FIG. 3 is an enlarged graph of the region around the point of origin of the graph of FIG. 2.

In FIG. 2 and as a detail enlargement in FIG. 3, two measurement curves of a methane measurement by the sensor 1 are shown. The first measurement curve 21 shows the course of the measuring signal $U_s$ in dependence upon the concentration of the combustible gas in the air mixture in percent by volume. It applies to the heat-tone measurement operating mode of the sensor 1. Its intersections with the abscissa are at the point of origin and at 100% by volume. Between the two it passes through a maximum.

The second measurement curve 22 shows the linear signal course of the measuring signal of the sensor 1 for the heat-conductivity measurement operating mode. The curve 22 begins at the origin of the coordinate system and shows an even negative slope. The reference values $R_1$, $R_2$ and the limit value G are marked on the ordinate. Their intersections with the corresponding measurement curves are at (23, 24) and at 25.

To start up the measuring device, the sensor 1 is first adjusted by the current source 2 to the operating temperature $T_1$ appropriate for heat-conductivity measurement. Its measured values lie on the calibration curve 22. If measured values below the limit value $R_1$ are received by the computer 5, the computer assembly 5, 6 recognizes that a lower concentration of combustible gas is present and the sensor is brought to an operating temperature $T_2$ which enables operation in the heat-tone measurement mode. All subsequent measurements will be on the basis of heat-tone measurement and will lie on the measurement curve 21. As long as the measuring signal $U_s$ remains below the limit value G, the sensor 1 remains in the heat-tone measurement operating mode. However, as soon as the measuring signal exceeds the limit value G, the computer assembly 5, 6 determines that concentrations of combustible gas have reached a level of, for example, above 5% by volume, and now causes the current source 2 to lower the operating temperature of the sensor 1 to the lower operating temperature $T_1$ required for the heat-conductivity measurement operating mode. If the concentration of combustible gas increases further, measurement is made along the measurement curve 22 identified by the thickened line portion thereof.

If the concentration of combustible gas falls below 5% by volume, the sensor 1 is again switched over to the heat-tone measurement operating mode and further measurement takes place along the thickly delineated portion of the measurement curve 21. In this way, there is alternate switching from one operating mode to the other depending on the concentration of the combustible gas.

If the operation is changed so that the measuring device is only switched over to the heat-tone measurement operating mode if a further reference value $R_2$ is exceeded, the comparator 6 checks whether the resultant measuring signals come within a window between $R_1$ and $R_2$.

In FIG. 2 the example of a methane measurement is shown, not to scale, where the concentration of 5% by volume corresponds to the 100% Lower Explosion Limit. The limit line of the Upper Explosion Limit is shown for information only, and also not to scale. The measurement of other combustible gases is carried out in an analogous fashion.

It is understood that the foregoing description is that of the preferred embodiments of the invention and that various changes and modifications may be made thereto without departing from the spirit and scope of the invention as defined in the appended claims.

What is claimed is:

1. Method for detecting the concentration of combustible gas contained in an air mixture with aid of a measuring device equipped with an indicating unit, the measuring device operating according to both the heat-tone process and the heat-conductivity process and to give an indication pursuant to the heat-tone process only beneath a predetermined reference value for the measuring signal, the method comprising the steps of:

at the start of measurement, holding a single individual sensor constant in said measuring device at a first temperature $T_1$ adequate for a heat-conductivity measurement, said sensor being catalytically active at a second temperature $T_2$ greater than said first temperature $T_1$ which enables a heat-tone measurement to be made;

obtaining a first signal from said sensor indicative of the concentration of combustible gas in said air mixture;

comparing the measuring signal emitted by said sensor with a first reference value $R_1$ corresponding to the presence of a predetermined concentration of the combustible gas;

increasing the temperature of the sensor to said second temperature $T_2$ only when said measuring signal indicates that combustible gas is present and at a concentration below said predetermined concentration corresponding to said reference value $R_1$ and holding the temperature of the sensor constant at said second temperature $T_2$ to obtain a second measuring signal indicative of the concentration of combustible gas in said air mixture, said sensor now operating as a heat-tone sensor;

comparing said second measuring signal emitted by said sensor with a load-limit value G corresponding to a concentration of the combustible gas higher than said value $R_1$; and, reducing the temperature of said sensor to said first temperature $T_1$ and holding the same constant as soon as said second measuring signal exceeds said load-limit value G to thereby again place said sensor in the heat-conductivity mode and obtain a further measuring signal indicative of the gas concentration of the combustible gas for concentrations thereof greater than that corresponding to said load-limit value G.

2. The method of claim 1, wherein said reference value $R_1$ and said load-limit value G lie approximately in the range of 100% to 140% of the lower explosion limit.

3. The method of claim 1, wherein said sensor signal emitted in response to the reduction of the temperature thereof to $T_1$ causes a full-scale reading of said indicator unit.

4. The method of claim 3, wherein said measuring device also includes an alarm unit and said last-mentioned signal also actuates said alarm unit.

5. Method for detecting the concentration of combustible gas contained in an air mixture with aid of a measuring device equipped with an indicating unit, the measuring device operating according to both the heat-tone process and the heat-conductivity process and to give an indication pursuant to the heat-tone process only beneath a predetermined reference value for the measuring signal, the method comprising the steps of:
at the start of measurement, holding a single individual sensor constant in said measuring device at a first temperature $T_1$ adequate for a heat-conductivity measurement, said sensor being catalytically active at a second temperature $T_2$ greater than said first temperature $T_1$ which enables a heat-tone measurement to be made;
obtainng a first signal from said sensor indicative of the concentration of combustible gas in said air mixture;
comparing said measuring signal emitted by said sensor with a first reference value $R_1$ corresponding to the presence of a first predetermined concentration of the combustible gas;
comparing said measuring signal with a second reference value $R_2$ corresponding to a second predetermined concentration of the combustible gas which lies beneath said first predetermined concentration of the gas corresponding to said first reference value $R_1$;
increasing the temperature of the sensor to said second temperature $T_2$ only when said measuring signal indicates that combustible gas is present and at a concentration which is below said predetermined concentration corresponding to said reference value $R_1$ and which also exceeds said reference value $R_2$ to obtain a second measuring signal indicative of the concentration of combustible gas in said air mixture, said sensor now operating as a heat-tone sensor;
comparing the measuring signal emitted by said sensor with a load-limit value G corresponding to a concentration of the combustible gas higher than said value $R_1$; and,
reducing the temperature of said sensor to said first temperature $T_1$ and holding the same constant as soon as said measuring signal exceeds load-limit value G to thereby again place said sensor in the heat-conductivity mode and obtain a further measuring signal indicative of the gas concentration of the combustible gas for concentrations thereof greater than that corresponding to said load-limit value G.

6. The method of claim 5, wherein the combustible gas is methane and wherein said first reference value $R_1$ or said load-limit value G correspond to 100 to 140 percent Lower Explosion Limit of said combustible gas and said second reference value $R_2$ lies in the range between 2 and 5 percent Lower Explosion Limit.

7. The method of claim 5, wherein said sensor signal emitted in response to the reduction of the temperature thereof to $T_1$ causes a full-scale reading of said indicator unit.

8. The method of claim 7, wherein said measuring device also includes an alarm unit and said last-mentioned signal also actuates said alarm unit.

9. A measuring device for detecting the concentration of combustible gas contained in an air mixture, the measuring device comprising:
single sensor means operable in both a heat-conductivity mode at a first temperature $T_1$ and a heat-tone mode at a second temperature $T_2$ greater than said first temperature $T_1$ and having a changeable sensor resistance;
a controllable current source connected to said sensor for controlling current supplied to the latter;
computer means connected to said sensor means for receiving an output signal thereof;
measuring means for measuring said sensor resistance and for providing a measurement signal indicative of said sensor resistance and of the concentration of combustible gas in said air mixture;
said computer means including a comparator for receiving said measurement signal for making a first comparison thereof with a first reference value $R_1$ corresponding to the presence of a first predetermined concentration of the combustible gas and for making a second comparison of said measuring signal with a second reference value $R_2$ corresponding to a second predetermined concentration of the combustible gas which lies beneath said first predetermined concentration of the gas corresponding to said first reference value $R_1$ and for issuing a first control signal to said current source only when said measuring signal indicates that combustible gas is present and at a concentration which is below said predetermined concentration corresponding to said reference value $R_1$ and which also exceeds said reference value $R_2$;
said current source being adapted to respond to said first control signal for providing an increased supply current to increase the temperature of the sensor to said second temperature $T_2$ to cause said sensor to operate as a heat-tone sensor;
said comparator also receiving said measurement signal for making a further comparison thereof to a load-limit value G corresponding to a concentration of the combustible gas higher than said value $R_1$ and for issuing a second control signal to said current source; and,
said current source also being adapted to respond to said second control signal for providing a reduced supply current to reduce the temperature of the sensor to said first temperature $T_1$ to cause said sensor to operate as a heat-conductivity sensor.

10. A measuring device for detecting the concentration of combustible gas contained in an air mixture, the measuring device comprising:
single sensor means operable in both a heat-conductivity mode at a first temperature $T_1$ and a heat-tone mode at a second temperature $T_2$ greater than said first temperature $T_1$ and having a changeable sensor resistance;
a controllable current source connected to said sensor for controlling current supplied to the latter;
computer means connected to said sensor means for receiving an output signal thereof;
measuring means for measuring said sensor resistance and for providing a measurement signal indicative of said sensor resistance and of the concentration of combustible gas in said air mixture;

said computer means including a comparator for receiving said measurement signal for making a comparison thereof with a first reference value $R_1$ corresponding to the presence of a predetermined concentration of the combustible gas and for issuing a first control signal to said current source only when said measuring signal indicates that combustible gas is present and at a concentration below said predetermined concentration corresponding to said reference value $R_1$;

said current source being adapted to respond to said first control signal for providing an incresaed supply current to increase the temperature of the sensor to said second temperature $T_2$ to cause said sensor to operate as a heat-tone sensor;

said comparator also receiving said measurement signal for making a further comparison thereof to a load-limit value G corresponding to a concentration of the combustible gas higher than said value $R_1$ and for issuing a second control signal to said current source; and, said current source also being adapted to respond to said second control signal for providing a reduced supply current to reduce the temperature of the sensor to said first temperature $T_1$ to cause said sensor to operate as a heat-conductivity sensor.

* * * * *

UNITED STATES PATENT AND TRADEMARK OFFICE
CERTIFICATE OF CORRECTION

PATENT NO. : 4,804,632

DATED : February 14, 1989

INVENTOR(S) : Hansjochen Schuck, Peter J. Iredale and Alan Johnson

It is certified that error appears in the above-identified patent and that said Letters Patent is hereby corrected as shown below:

On the front page one reference cited was missing. Under "U.S. Patent Documents", add -- 4,664,886 5/87 Novack et al... ...422/94 --.

In column 1, line 9: insert -- the -- after "both".

In column 4, line 9: delete "as" and substitute -- at -- therefor.

In column 7, line 23: delete "obtainng" and substitute -- obtaining -- therefor.

In column 9, line 13: delete "incresaed" and substitute -- increased -- therefor.

Signed and Sealed this

Twentieth Day of June, 1989

Attest:

DONALD J. QUIGG

Attesting Officer

Commissioner of Patents and Trademarks